United States Patent [19]

Demus et al.

[11] Patent Number: 4,734,217
[45] Date of Patent: Mar. 29, 1988

[54] LIQUID CRYSTALLINE 2,6-DISUBSTITUTED-TRANS-1,3-DIOXADECALINS

[75] Inventors: Dietrich Demus; Horst Zaschke; Carsten Tschierske, all of Halle; Maike Hettrich, Berlin, all of German Democratic Rep.

[73] Assignee: VEB Werk fuer Fernsehelektronik im VEB Kombinat Mikroelektronik, Berlin, German Democratic Rep.

[21] Appl. No.: 780,489

[22] Filed: Sep. 26, 1985

[30] Foreign Application Priority Data

Oct. 16, 1984 [DE] Fed. Rep. of Germany ....... 2684130
Oct. 16, 1984 [DE] Fed. Rep. of Germany ....... 2684122

[51] Int. Cl.$^4$ ...................... C09K 19/34; C09K 19/32; G02F 1/13; C07D 319/08
[52] U.S. Cl. ................................ 252/299.61; 549/365; 252/299.62; 252/299.5; 350/350 R; 350/350 S
[58] Field of Search .................... 549/365; 252/299.61, 252/299.62, 299.5; 350/350 R, 350 S

[56] References Cited

U.S. PATENT DOCUMENTS

| | | | |
|---|---|---|---|
| 4,344,856 | 8/1982 | Demus et al. | 252/299.61 |
| 4,348,324 | 9/1982 | Demus et al. | 549/369 |
| 4,386,007 | 5/1983 | Krause et al. | 252/299.62 |
| 4,432,885 | 2/1984 | Petrazilka et al. | 252/299.61 |
| 4,438,268 | 3/1984 | Zaschke et al. | 544/315 |
| 4,439,015 | 3/1984 | Rich et al. | 350/350 R |
| 4,462,923 | 7/1984 | Boller et al. | 252/299.61 |
| 4,486,332 | 12/1984 | Demus et al. | 252/299.61 |
| 4,600,528 | 7/1986 | Eidenschink et al. | 252/299.61 |

FOREIGN PATENT DOCUMENTS

| | | | |
|---|---|---|---|
| 87679 | 9/1983 | European Pat. Off. | 252/299.61 |
| 3328638 | 2/1985 | Fed. Rep. of Germany | 252/299.61 |
| 3335244 | 4/1985 | Fed. Rep. of Germany | 252/299.61 |
| 227719 | 9/1985 | German Democratic Rep. | 252/299.61 |

Primary Examiner—Teddy S. Gron
Assistant Examiner—J. E. Thomas
Attorney, Agent, or Firm—Jordan and Hamburg

[57] ABSTRACT

Liquid crystalline 2,6-disubstituted trans-1,3-dioxadecalins of the general formula

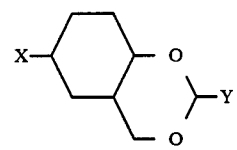

(I)

are well suited as components of low double refraction for mixtures which are utilized in opto-electronic components.

40 Claims, No Drawings

LIQUID CRYSTALLINE 2,6-DISUBSTITUTED-TRANS-1,3-DIOXADECALINS

BACKGROUND OF THE INVENTION

The invention relates to liquid crystalline 2,6-disubstituted-trans-1,3-dioxadecalins, a method for the production of the compounds and their utilization in liquid crystal mixtures.

Liquid crystalline nematic substances are used as dielectrics in opto-electronic displays of various constructions /H. Kelker, R. Hatz: Handbook of Liquid Crystals, publishing firm Chemie 1980/.

In recent years, many new application purposes have been proposed, whereby displays of very specific properties are required. No pure substances are known which could even only approximately meet the technical requirements of the art. For this reason there are always used mixtures of liquid crystalline substances, which have the advantage that by suitable selection of the components of the mixture, it is possible to modify the properties within a great range and thus to adjust them to specific application purposes.

For mixtures intended for the guest-host effect, there are particularly advantageous mixtures of low optical double refraction ($\Delta n$). Mixtures for the Schadt-Helfrich luminosity impart to the displays advantageous properties with respect to the information's readability at shallow angles, if the mixtures have a low optical double refraction. Because the double refraction of a mixture is approximately the additive product of the values of the pure components, in order to attain mixtures of low double refraction, substances of low double refraction values are a necessary prerequisite.

The object of the invention is to find substances which impart a low optical double refraction to liquid crystalline nematic mixtures which are utilized in opto-electronic components.

SUMMARY OF THE INVENTION

It has been found that liquid crystalline 2,6-disubstituted trans-1,3-dioxadecalins of the general formula

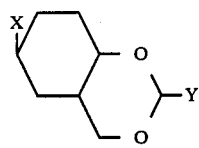

(I)

wherein
X=H and Y=$R^1$
or
X=$R^2$ and Y=$R^1$, $R^3$
wherein

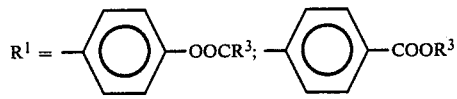

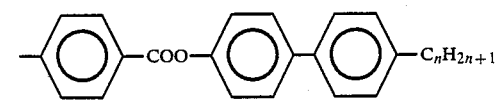

$R^2 = C_nH_{2n+1}$

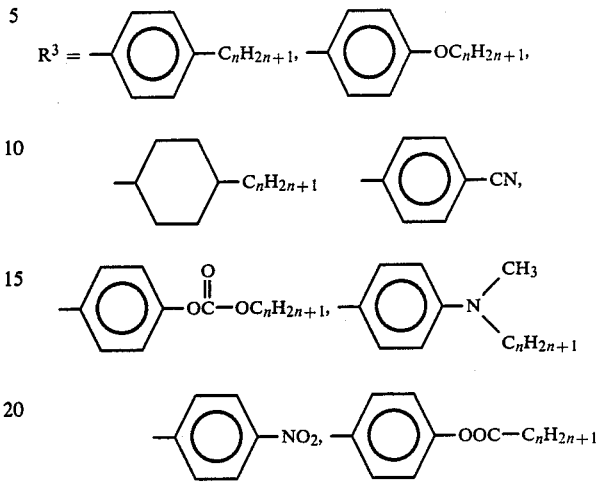

wherein n=1 to 10, are well suited as components of low double refraction for mixtures which are utilized in opto-electronic components.

According to the invention, liquid crystalline 2,6-disubstituted trans-1,3-dioxadecalins are produced by reaction of alkanols, substituted benzaldehydes, substituted cyclohexanecarbaldehydes or the acetals thereof with trans-2-hydroxymethylcyclohexanol or 4(e)-alkyl-1(e)hydroxy-2(e)-hydroxymethylcyclohexanes, which are obtained by reaction of metal enolates of the 4-alkylcyclohexanones with gaseous formaldehyde, equilibration of the 4-alkyl-2-hydroxymethyl-cyclohexanones and subsequent reduction with complex hydrides, in organic solvents in the presence of an acid catalyst, for example $H_2SO_4$, HCl, $H_3PO_4$, p-toluenesulfonic acid, $AlCl_3$, $BF_3.Et_2O$ according to the general scheme 1:

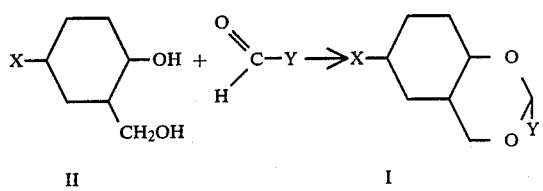

The up to now not known 4(e)-alkyl-1(e)-hydroxy-2-(e)-hydroxymethylcyclohexanes (II) are obtained in pure form by reduction of a mixture of the stereoisomer 4-alkyl-2-hydroxymethylcyclohexanones (III) with complex hydrides, preferably $LiAlH_4$, and subsequent fractional crystallization from organic solvents, for example benzene, petroleum ether or n-hexane.

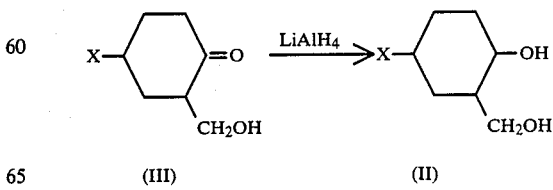

The 4-alkyl-2-hydroxymethylcyclohexanones (III) are synthesized according to scheme 2:

Scheme 2:

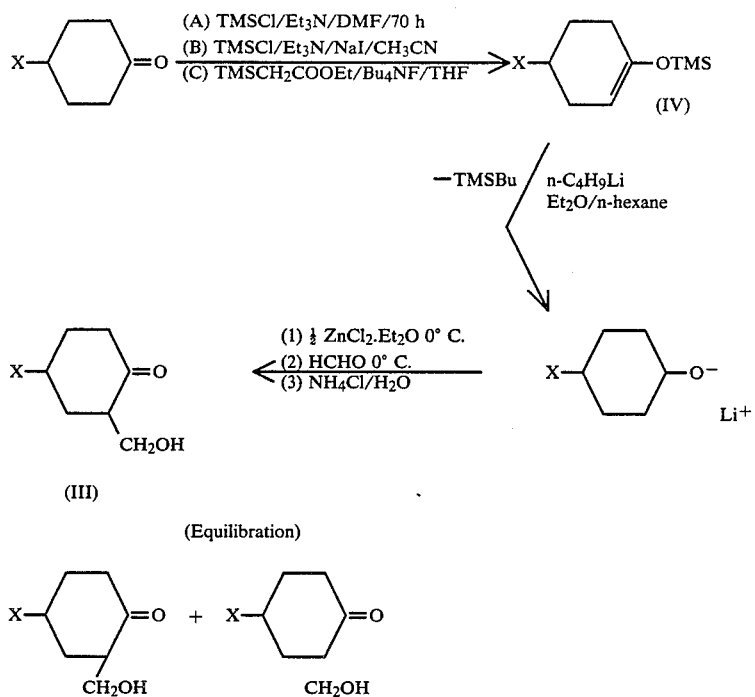

(Equilibration)

DETAILED DESCRIPTION OF PREFERRED EMBODIMENTS

The production of the substances according to the invention will be explained by an example.

Production of the 4-alkyl-1-trimethylsilyloxycyclohex-1-enes (IV) (variant B)

In a 500 ml three-necked flask, under exclusion of moisture, to a solution of 65 g (0.43 mol) NaI, 44 g (0.43 mol) triethylamine and 0.35 mol 4-alkyl-cyclohexanone in 350 ml absolute acetonitrile is dropwise added under ice-cooling and stirring 48 g (0.43 mol) trimethyl silane chloride (TMSCl) at room temperature. Subsequently follows stirring for 20 minutes at 25° C., the solvent is distilled off in vacuum, the solid residue is mixed with 200 ml petroleum ether and is filtered off from the insoluble residue. The latter is washed five times with 100 ml petroleum ether each. The petroleum ether solutions are reduced in vacuum and the silylenol ether (IV) is fractionally distilled in vacuum.

The following table shows the yields of the various silylenol ethers (IV).

| n | Yield (%) | B.P. °C./Torr |
|---|---|---|
| 4 | 91 | 72/0.08 |
| 5 | 91 | 82/0.06 |
| 6 | 96 | 92 . . . 93/0.06 |

For the production of the 4-alkyl-2-hydroxymethyl-cyclohexanones (III), to a solution of 0.1 mol 4-alkyl-1-trimethylsilyloxycyclohex-1-ene (IV) and 10 mg α,α'-dipyridyl in 50 ml absolute ether, under stirring and ice-cooling in an argon atmosphere is dropwise added 110 ml of a 1.0 molar solution of n-butyllithium in n-pentane at 20° to 25° C. within ¼ hour. After stirring for 1 to 2 hours at this temperature the reaction mixture is cooled down to 0° C. and at this temperature is dropwise added 110 ml of a 0.5-molar $ZnCl_2$ solution in anhydrous ether. The reaction mixture is stirred for approximately 20 minutes at 0° to 10° C. Subsequently, under 5 minutes of vigorous stirring and cooling at $-10°$ C. to 0° C., 4 g gaseous formaldehyde is conducted in an argon stream onto the surface of the reaction mixture. The formaldehyde is produced by depolymerization of α-polyoxymethylene in the argon stream at 175° C. For purification, the formaldehyde is conducted through a 6 m long, 1 cm wide glass tube before it reaches the reaction vessel.

The reaction mixture is immediately poured into a 500 ml solution containing 20% $NH_4Cl$ and is shaken until the precipitate is dissolved.

The organic phase is separated and the aqueous phase is ethered out twice. The combined organic phases are washed successively with $NH_4Cl$ solution and water, dried over $Na_2SO_4$, the solvent is distilled off at the rotary evaporator and the residue is twice fractionally distilled in vacuum, whereby the product equilibrates. The table indicates yields of various cyclohexanones (III).

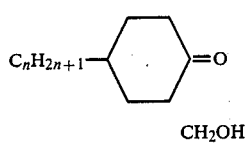

(III)

| n | Yield (%) | B.P. (°C./Torr) |
|---|---|---|
| 4 | 60 | 87–90/0.02 |
| 5 | 43 | 117/0.06 |
| 6 | 40 | 125/0.08 |

For the production of the 4(e)-alkyl-1(e)-hydroxy-2(e)-hydroxymethylcyclohexanes (II) are prepared in a 500 ml three-necked flask 2.1 g (0.05 mol) LiAlH$_4$ in 250 ml absolute ether.

Under ice-cooling and vigorous stirring 0.05 mol 4-alkyl-2-hydroxymethylcyclohexanone (III) dissolved in 50 ml absolute ether is slowly dropwise added and subsequently stirred under reflux for 2 hours. Subsequently, the solution is carefully hydrolyzed with 25 ml H$_2$O, the resulting precipitate is dissolved by adding 150 ml of 10% H$_2$SO$_4$.

The organic phase is separated, the aqueous phase is ethered out three times and the combined organic phases are washed with a solution containing 2% NaHCO$_3$ and H$_2$O.

After drying with Na$_2$SO$_4$ the solvent is distilled off in vacuum and the residue is dissolved in 50 ml n-hexane. The solution is cooled down to 0° C. to 20° C., the crystalline precipitate is suctioned off and purified by repeated recrystallizations from n-hexane.

The table indicates the yields of various cyclohexanes (II).

(II)

| n | Yield (%) | B.P. (°C./Torr) | Solidification Point |
|---|---|---|---|
| 5 | 20 | 117/0.05 | 62–64 (°C.) |
| 6 | 25 | 146/0.25 | 65–67 |

For the production of the 2,6-disubstituted trans-1,3-dioxadecalins (I) 5 mmol alkanol or substituted benzaldehyde and 5 mmol 4(e)-alkyl-1(e)-hydroxy-2(e)-hydroxymethylcyclohexane (II) or trans-2-hydroxymethylcyclohexanol in 150 ml benzene or CHCl$_3$, CH$_2$Cl$_2$, CCl$_4$ or toluene in the presence of 50 ml p-toluenesulfonic acid are heated in the water separator until the reaction is completed. After cooling of the reaction mixture follows washing with saturated NaHCO$_3$ solution and H$_2$O and drying over Na$_2$SO$_4$. The solvent is distilled off in the rotary evaporator and the residue is recrystallized from methanol, ethanol or n-hexane until melting point and clarification point constancy is attained. The yields of (I) amount 70 to 95% of the theoretical.

In the tables 1–4 are indicated the transformation temperatures for the produced substances.
In the tables
K = crystalline solid
S$_A$ = smectic A
N = nematic
I = isotropic liquid.

TABLE 1

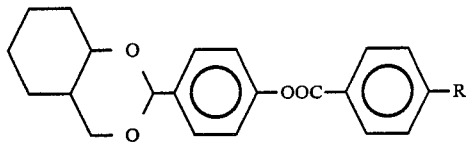

| Compound | R | K | N | I |
|---|---|---|---|---|
| 1/1 | CH$_3$ | . 137 | (. 69) | . |
| 1/2 | C$_2$H$_5$ | . 122 | (. 80) | . |
| 1/3 | C$_3$H$_7$ | . 111 | (. 90) | . |
| 1/4 | C$_4$H$_9$ | . 103 | (. 91.5) | . |
| 1/5 | C$_5$H$_{11}$ | . 95 | (. 84) | . |
| 1/6 | C$_6$H$_{13}$ | . 112.5 | (. 66) | . |
| 1/7 | OCH$_3$ | . 151.5 | (. 118.5) | . |
| 1/8 | OC$_2$H$_5$ | . 112 | . 135 | . |
| 1/9 | OC$_3$H$_7$ | . 113 | (. 112.5) | . |
| 1/10 | OC$_4$H$_9$ | . 94 | . 115 | . |
| 1/11 | OC$_5$H$_{11}$ | . 96 | . 99 | . |
| 1/12 | OC$_6$H$_{13}$ | . 98 | . 99.5 | . |
| 1/13 | OC$_7$H$_{15}$ | . 96 | (. 92) | . |
| 1/14 | OC$_8$H$_{17}$ | . 68 | . 97.2 | . |
| 1/15 | OC$_9$H$_{19}$ | . 77 | . 89.3 | . |
| 1/16 | OC$_{10}$H$_{21}$ | . 82 | . 89 | . |
| 1/17 | CN | . 193 | — — | . |

TABLE 2

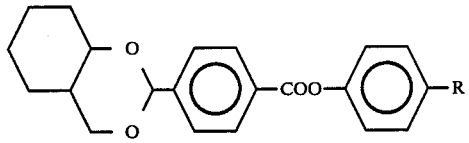

| Compound | R | K | N | I |
|---|---|---|---|---|
| 2/1 | —C$_5$H$_{11}$ | . 87.5 | (. 70) | . |
| 2/2 | —C$_6$H$_{13}$ | . 77.5 | (. 56.8) | . |
| 2/3 | C$_6$H$_{13}$—⟨⟩— | . 97 | . 214 | . |
| 2/4 | —OC$_5$H$_{11}$ | . 93 | . 94.5 | . |
| 2/5 | —OC$_6$H$_{13}$ | . 82 | . 98 | . |

TABLE 3

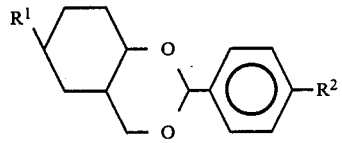

| Compound | R$^1$ | R$^2$ | K | S$_A$ | N | I |
|---|---|---|---|---|---|---|
| 3/1 | —C$_5$H$_{11}$ | —OC$_3$H$_7$ | . 77.5 | — — | (. 63.5) | . |
| 3/2 | —C$_5$H$_{11}$ | —C$_4$H$_9$ | . 77 | — — | (. 74.0) | . |
| 3/3 | —C$_5$H$_{11}$ | —OC$_5$H$_{11}$ | . 61 | — — | . 70 | . |
| 3/4 | —C$_5$H$_{11}$ | —C$_4$H$_9$ | . 61 | (. 31) | — — | . |
| 3/5 | —C$_5$H$_{11}$ | —OOC—CH$_3$ | . 90 | — — | (. 55.5) | . |
| 3/6 | —C$_5$H$_{11}$ | —OOC—C$_2$H$_5$ | . 86 | — — | (. 78) | . |
| 3/7 | —C$_5$H$_{11}$ | —OOC—C$_5$H$_{11}$ | . 79 | — — | . 79.2 | . |
| 3/8 | —C$_5$H$_{11}$ | —CN | . 87 | — — | (. 85) | . |
| 3/9 | —C$_6$H$_{13}$ | —C$_4$H$_9$ | . 53.5 | (. 36) | — — | . |
| 3/10 | —C$_6$H$_{13}$ | —CN | . 87 | — — | (. 80) | . |

TABLE 4

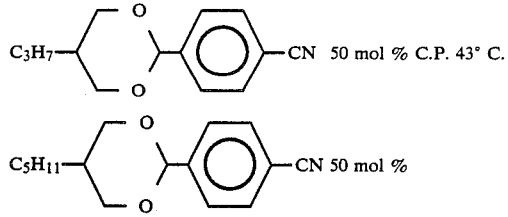

| Compound | R¹ | R² | K | $S_A$ | N | I |
|---|---|---|---|---|---|---|
| 4/1 | C₅H₁₁ | C₆H₁₃ | . 58 | . 83 | . 94 | . |
| 4/2 | C₆H₁₃ | C₆H₁₃ | . 54 | . 87.9 | . 88.1 | . |

The following examples are intended for the demonstration of the desired properties of the substances according to the invention in liquid crystalline mixtures.

EXAMPLE I

In some substances according to the invention the optical double refraction $\Delta n$ for light of the wavelength 589 nm per 10° K. below the clarification point as well as the melting enthalpy $\Delta H$ have been measured.

| Substance No. | $\Delta n$ | $\Delta H/kJ \cdot mol^{-1}$ |
|---|---|---|
| 4/2 | 0.045 | 33.1 |
| 3/3 | 0.056 | 34.9 |
| 4/1 | 0.0335 | 40.8 |

The measured double refractions are extremely small, liquid crystals predominantly have values $\Delta n > 0.1$ /H. Kelker, R. Katz, Handbook of Liquid Crystals, publishing firm Chemie 1980/.

EXAMPLE II

The influence of the substances according to the invention on electro-optical properties of mixtures can be seen from the following chart.

A mixture Mi 14, consisting of

| | |
|---|---|
| 4-n-propyl-cyclohexane carboxylic acid-4-cyanophenylester | 34.5 mol % |
| 4-n-butyl-cyclohexane carboxylic acid-4-cyanophenylester | 31 mol % |
| 4-n-pentyl-cyclohexane carboxylic acid-4-cyanophenylester | 34.5 mol % | changed its properties as follows:

| Mi 14 mol % | Subst. No. | mol % | C.P. | $U_o$ V | U = $2U_o$ V | $\tau_{50}$ $E_{ms}$ | $\tau_{50}$ $A_{ms}$ | $\eta^d$ | $\mu m$ |
|---|---|---|---|---|---|---|---|---|---|
| 100 | — | — | 72.0 | 1.3 | 2.6 | 580 | 200 | 33.0 | 24.0 |
| 90 | 4/1 | 10 | 73.0 | 1.4 | 2.8 | 750 | 350 | 46.5 | 21.7 |
| 90 | 4/2 | 10 | 73.5 | 1.4 | 2.8 | 680 | 150 | 46.7 | 20.0 | wherein
C.P.—Clarification point in °C.
$U_o$—Threshold voltage at 20° C., 500 Hz
U—Operating voltage
$\tau_E 50$—Switching on time at 50% change of intensity 20° C. 500 Hz
$\tau_A 50$—Decay period at 50% change of intensity 20° C., 500 Hz
d—Thickness of layer
$\eta$—Viscosity at 20° C. in cP

EXAMPLE III

To a mixture of dioxane derivatives of the following composition

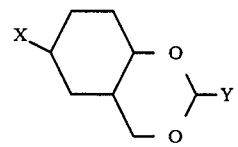

20 mol-% each substance has been added.
Thereby resulted the following changes of the clarification point:

| added substance (No.) | Clarification point (°C.) |
|---|---|
| 4/2 | 50 |
| 4/1 | 58 |

We claim:
1. Liquid crystalline 2,6-disubstituted trans-1,3-dioxadecalins of the general formula

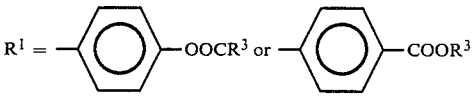

wherein
X=H and Y=R¹
or
X=R² and Y=R³
and

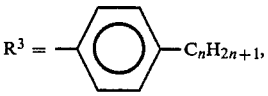

$R^2 = C_nH_{2n+1}$

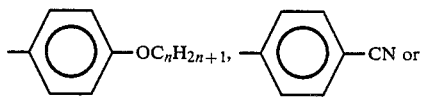

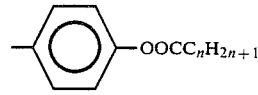

wherein n=1 to 10.

2. 2,6-disubstituted trans-1,3-dioxadecalins according to claim 1, in which

X = H and Y = 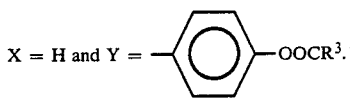

3. 2,6-disubstituted trans-1,3-dioxadecalins according to claim 1 or 2, in which

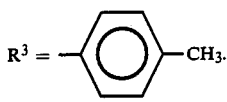

4. 2,6-disubstituted trans-1,3-dioxadecalins according to claim 1 or 2, in which

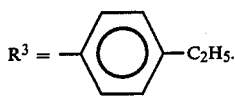

5. 2,6-disubstituted trans-1,3-dioxadecalins according to claim 1 or 2, in which

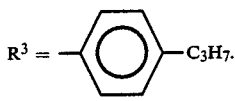

6. 2,6-disubstituted trans-1,3-dioxadecalins according to claim 1 or 2, in which

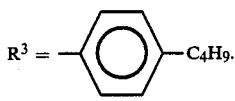

7. 2,6-disubstituted trans-1,3-dioxadecalins according to claim 1 or 2, in which

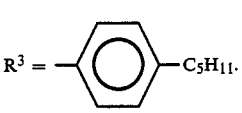

8. 2,6-disubstituted trans-1,3-dioxadecalins according to claim 1 or 2, in which

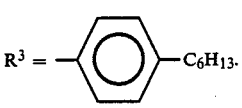

9. 2,6-disubstituted trans-1,3-dioxadecalins according to claim 1 or 2, in which

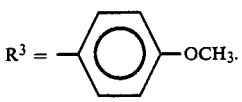

10. 2,6-disubstituted trans-1,3-dioxadecalins according to claim 1 or 2, in which

11. 2,6-disubstituted trans-1,3-dioxadecalins according to claim 1 or 2, in which

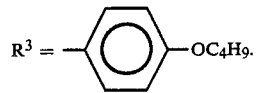

12. 2,6-disubstituted trans-1,3-dioxadecalins according to claim 1 or 2, in which

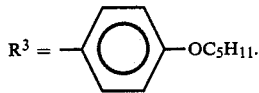

13. 2,6-disubstituted trans-1,3-dioxadecalins according to claim 1 or 2, in which

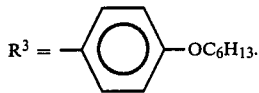

14. 2,6-disubstituted trans-1,3-dioxadecalins according to claim 1 or 2, in which

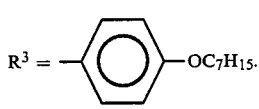

15. 2,6-disubstituted trans-1,3-dioxadecalins according to claim 1 or 2, in which

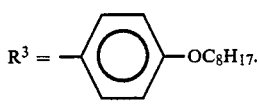

16. 2,6-disubstituted trans-1,3-dioxadecalins according to claim 1 or 2, in which

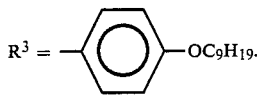

17. 2,6-disubstituted trans-1,3-dioxadecalins according to claim 1 or 2, in which $R^3 = $ —⟨O⟩— $OC_9H_{19}$.

18. 2,6-disubstituted trans-1,3-dioxadecalins according to claim 1 or 2, in which

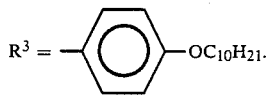 $R^3 = $ —⟨O⟩— $OC_{10}H_{21}$.

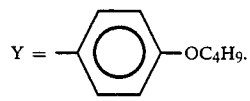 $Y = $ —⟨O⟩— $OC_4H_9$.

19. 2,6-disubstituted trans-1,3-dioxadecalins according to claim 1 or 2, in which

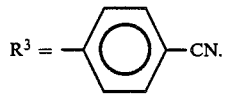 $R^3 = $ —⟨O⟩— CN.

27. 2,6-disubstituted trans-1,3-dioxadecalins according to claim 1, in which X=pentyl and

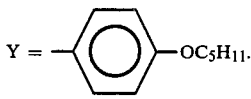 $Y = $ —⟨O⟩— $OC_5H_{11}$.

20. 2,6-disubstituted trans-1,3-dioxadecalins according to claim 1, in which

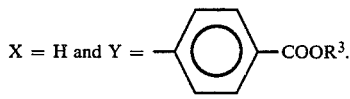 X = H and Y = —⟨O⟩— $COOR^3$.

28. 2,6-disubstituted trans-1,3-dioxadecalins according to claim 1, in which X=pentyl and

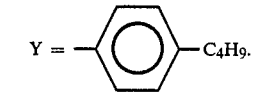 $Y = $ —⟨O⟩— $C_4H_9$.

21. 2,6-disubstituted trans-1,3-dioxadecalins according to claim 1 or 20, in which

29. 2,6-disubstituted trans-1,3-dioxadecalins according to claim 1, in which X=pentyl and

 $R^3 = $ —⟨O⟩— $C_5H_{11}$.

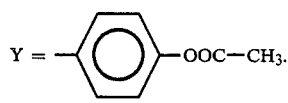 $Y = $ —⟨O⟩— $OOC-CH_3$.

22. 2,6-disubstituted trans-1,3-dioxadecalins according to claim 1 or 20, in which

30. 2,6-disubstituted trans-1,3-dioxadecalins according to claim 1, in which X=pentyl and

 $R^3 = $ —⟨O⟩— $C_6H_{13}$.

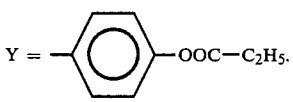 $Y = $ —⟨O⟩— $OOC-C_2H_5$.

23. 2,6-disubstituted trans 1,3-dioxadecalins according to claim 1 or 20, in which

31. 2,6-disubstituted trans-1,3-dioxadecalins according to claim 1, in which X=pentyl and

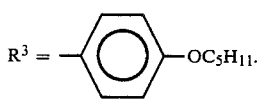 $R^3 = $ —⟨O⟩— $OC_5H_{11}$.

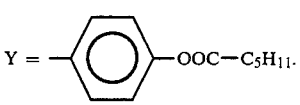 $Y = $ —⟨O⟩— $OOC-C_5H_{11}$.

24. 2,6-disubstituted trans-1,3-dioxadecalins according to claim 1 or 20, in which

32. 2,6-disubstituted trans-1,3-dioxadecalins according to claim 1, in which X=pentyl and

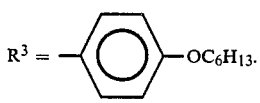 $R^3 = $ —⟨O⟩— $OC_6H_{13}$.

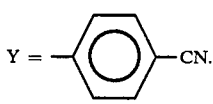 $Y = $ —⟨O⟩— CN.

25. 2,6-disubstituted trans-1,3-dioxadecalins according to claim 1, in which X=pentyl and

33. 2,6-disubstituted trans-1,3-dioxadecalins according to claim 1, in which X=hexyl and

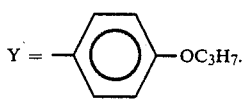 $Y = $ —⟨O⟩— $OC_3H_7$.

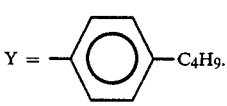 $Y = $ —⟨O⟩— $C_4H_9$.

26. 2,6-disubstituted trans-1,3-dioxadecalins according to claim 1, in which X=pentyl and

34. 2,6-disubstituted trans-1,3-dioxadecalins according to claim 1, in which X=hexyl and

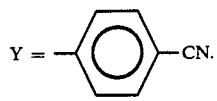

35. 2,6-disubstituted trans-1,3-dioxadecalins according to claim 1, in which X=pentyl and

36. 2,6-disubstituted trans-1,3-dioxadecalins according to claim 1, in which X=hexyl and

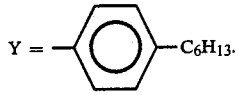

37. Nematic liquid crystalline mixtures comprising at least one nematic liquid crystalline compound according to claim 1 and at least one other liquid crystalline compound.

38. A liquid crystal display containing a compound according to claim 1.

39. A liquid crystal display containing a mixture according to claim 37.

40. Liquid crystalline 2,6-disubstituted trans-1,3-dioxadecalins of the general formula

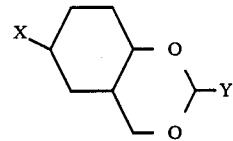

wherein X=H;

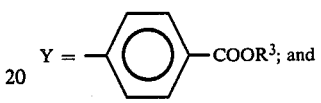

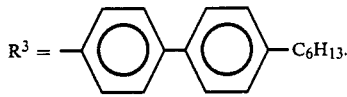

* * * * *

UNITED STATES PATENT AND TRADEMARK OFFICE
CERTIFICATE OF CORRECTION

PATENT NO. : 4,734,217
DATED : March 29, 1988
INVENTOR(S) : Dietrich Demus et al It is certified that error appears in the above-identified patent and that said Letters Patent are hereby corrected as shown below:

Title page:

[30] Foreign Application Priority Data

"Fed. Rep. of Germany" both occurrences should read

--German Democratic Republic--

Signed and Sealed this

Sixth Day of September, 1988

Attest:

DONALD J. QUIGG

*Attesting Officer*

*Commissioner of Patents and Trademarks*